(12) United States Patent
Wolfgramm et al.

(10) Patent No.: US 11,883,574 B2
(45) Date of Patent: Jan. 30, 2024

(54) MODULAR HEATER COOLER WITH DISPOSABLE HEAT TRANSFER FLUID CIRCUIT

(71) Applicant: LivaNova Deutschland GmbH, Munich (DE)

(72) Inventors: Olivier Wolfgramm, Munich (DE); Michael Bonczar, Ampfing (DE)

(73) Assignee: LivaNova Deutschland GmbH, Munich (DE)

( * ) Notice: Subject to any disclaimer, the term of this patent is extended or adjusted under 35 U.S.C. 154(b) by 779 days.

(21) Appl. No.: 16/753,750

(22) PCT Filed: Oct. 6, 2017

(86) PCT No.: PCT/EP2017/075473
§ 371 (c)(1),
(2) Date: Apr. 3, 2020

(87) PCT Pub. No.: WO2019/068342
PCT Pub. Date: Apr. 11, 2019

(65) Prior Publication Data
US 2020/0276376 A1    Sep. 3, 2020

(51) Int. Cl.
 *A61M 1/36*    (2006.01)
 *A61M 1/16*    (2006.01)
 (Continued)

(52) U.S. Cl.
 CPC ........ *A61M 1/1698* (2013.01); *A61M 1/3623* (2022.05); *A61M 1/3666* (2013.01); *F28D 7/082* (2013.01); *A61M 2205/3368* (2013.01); *A61M 2205/3606* (2013.01); *A61M 2205/366* (2013.01); *A61M 2205/3673* (2013.01); *F28D 2021/005* (2013.01)

(58) Field of Classification Search
 CPC .. A61M 1/1698; A61M 1/3666; A61M 1/369; A61M 2205/3368;
 (Continued)

(56) References Cited

U.S. PATENT DOCUMENTS 4,476,867 A * 10/1984 Parks .................. A61M 1/3655
165/61
4,559,999 A   12/1985 Servas et al.
(Continued)

FOREIGN PATENT DOCUMENTS

CN        1857745 A       11/2006
DE    102014116601 A1      5/2016
(Continued)

*Primary Examiner* — Benjamin J Klein
(74) *Attorney, Agent, or Firm* — Seager, Tufte & Wickhem LLP

(57) ABSTRACT

A system (20) including a heater/cooler module (22) to heat/cool a first fluid in a primary circuit (28), a heat transfer fluid circuit (24) to provide a second fluid to a target device (38) to heat/cool the target device (38), and a heat exchanger (26) including at least part of the primary circuit (28) and at least part of a secondary circuit (36) through which the second fluid flows to facilitate heat transfer between the first fluid and the second fluid. The primary circuit (28) and the secondary circuit (36) are separate circuits and the first fluid and the second fluid remain separated in the system. Also, the system is modular, such that the elements can be stacked to increase heating/cooling capability and/or to increase the number of heating/cooling channels, and the system is compatible with portable applications, such as ambulance, aircraft, and helicopter applications, and with battery operation and/or the use of uninterruptible power supplies.

18 Claims, 8 Drawing Sheets

(51) Int. Cl.
*F28D 7/08* (2006.01)
*F28D 21/00* (2006.01)

(58) Field of Classification Search
CPC .... A61M 2205/3606; A61M 2205/366; A61M 2205/3673; F28D 7/0008; F28D 7/082; F28D 15/00; F28D 2021/005; F28D 2021/0077; F28F 3/12; F28F 27/00
See application file for complete search history.

(56) References Cited

U.S. PATENT DOCUMENTS

| | | |
|---|---|---|
| 2003/0045917 A1 | 3/2003 | Noda et al. |
| 2007/0197951 A1* | 8/2007 | Mannlein ................ A61M 5/44 604/6.13 |
| 2012/0029408 A1* | 2/2012 | Beaudin ................ A61M 1/369 604/4.01 |
| 2014/0172050 A1* | 6/2014 | Dabrowiak ............... A61F 7/12 607/106 |
| 2014/0358201 A1 | 12/2014 | Scott et al. |
| 2015/0151073 A1* | 6/2015 | Shushunov ........... A61M 16/10 128/204.15 |
| 2017/0267907 A1 | 9/2017 | Knott et al. |
| 2019/0209762 A1* | 7/2019 | Turner ................ A61M 1/3666 |

FOREIGN PATENT DOCUMENTS

| | | |
|---|---|---|
| EP | 3655058 B1 | 6/2021 |
| EP | 3478336 B1 | 7/2022 |
| JP | H06237993 A | 8/1994 |
| WO | 2017042319 A1 | 3/2017 |
| WO | 2018099593 A1 | 6/2018 |

\* cited by examiner

MODULAR HEATER COOLER WITH DISPOSABLE HEAT TRANSFER FLUID CIRCUIT

CROSS REFERENCE TO RELATED APPLICATION

This application is a national stage application of PCT/EP2017/075473, filed Oct. 6, 2017, which is herein incorporated by reference in its entirety.

TECHNICAL FIELD

The present disclosure relates to a system for heating and/or cooling (heating/cooling) a target device. More specifically, the disclosure relates to a system for heating/cooling a patient or organs or other fluids, like blood, either directly or through a secondary fluid circuit, e.g., a heat exchanger, in an oxygenator of a heart-lung machine during extracorporeal blood circulation.

BACKGROUND

Oxygenators are devices used for extracorporeal oxygenation of blood. Often, oxygenators are used in heart-lung machines or extracorporeal membrane oxygenation (ECMO) devices, which include membrane oxygenators that can avoid embolisms to a large extent. With the aid of gas mixers and flow meters the transfer of oxygen and carbon dioxide is reliably controlled.

In an oxygenator, a patient's blood is warmed or cooled and oxygenated. The oxygenator includes a heat exchanger for warming or cooling the blood. In the oxygenator, a heat exchanging medium flows through the heat exchanger and transfers a heat quantity to the blood for warming the blood or absorbs a heat quantity from the blood for cooling the blood. The heat exchanging medium is usually supplied to the heat exchanger by a pump unit and, after heat exchange with the blood has taken place, the heat exchanging medium is discharged from the heat exchanger by the same pump unit or another pump unit. The heat exchanging medium, e.g. water, is previously heated or cooled in a heater/cooler before it is conducted to the heat exchanger. Due to its size and complex structure, the heater/cooler is separate from the heart-lung machine or ECMO.

In some situations, where not properly cleaned or maintained, the heat exchange medium of the heater/cooler may have contamination issues. In this situation, the heater/cooler may present a risk that the equipment and/or atmosphere in the OR may be contaminated and that germs will enter the patient's blood from the contaminated heat exchanging medium. Also, the heater/cooler may be over powered for most applications and present power consumption and power supply compatibility issues. In addition, due to its large size, the heater/cooler may have limited usability and may not be transportable. Also, due to its size to power ratio the heater/cooler may not be suited for intensive care unit (ICU) applications.

SUMMARY

The present invention relates to heater/cooler configurations that advantageously eliminate the need for a fluid reservoir (often open to the atmosphere) holding the heat exchanging medium. Further these configurations provide for two distinct fluid circuits, a first circuit which is heated by the heater/cooler device and a second circuit in communication with the target device (e.g., the heat exchanger). Thus, in the event the heat exchange medium should become contaminated, any such contamination cannot is not communicated to the target device and thus cannot contaminate the patient's blood.

As recited in examples, example 1 is a system including a heater/cooler module including a primary circuit and configured to heat/cool a first fluid in the primary circuit, a heat transfer fluid circuit configured to provide a second fluid to a target device to heat/cool the target device, and a heat exchanger including at least part of the primary circuit through which the first fluid flows and at least part of a secondary circuit through which the second fluid flows to facilitate heat transfer between the first fluid and the second fluid. The primary circuit and the secondary circuit are separate circuits, such that the first fluid and the second fluid remain separated in the system.

Example 2 is the system of example 1, wherein the primary circuit is a permanent part of the heater/cooler module.

Example 3 is the system of example 1, wherein the primary circuit is a hermetically sealed closed circuit containing the first fluid.

Example 4 is the system of example 1, wherein the at least part of the secondary circuit is part of the heater/cooler module and non-disposable, such that the at least part of the secondary circuit is cleaned and disinfected after one or more uses.

Example 5 is the system of example 1, wherein the secondary circuit is part of the heat transfer fluid circuit.

Example 6 is the system of example 1, wherein the secondary circuit is part of the heat transfer fluid circuit and disposable.

Example 7 is the system of example 1, wherein the heat transfer fluid circuit is a single use disposable circuit.

Example 8 is the system of example 1, wherein the heat transfer fluid circuit is a reusable circuit that is cleaned and disinfected after one or more uses.

Example 9 is the system of example 1, including at least one of two or more heat exchangers, two or more heater/cooler modules, and two or more heat transfer fluid circuits.

Example 10 is the system of example 1, wherein the secondary circuit is a hermetically sealed closed circuit containing the second fluid.

Example 11 is the system of example 1, wherein the heater/cooler module includes a heat pump to heat/cool the first fluid in the primary circuit.

Example 12 is the system of example 1, wherein the heater/cooler module includes an auxiliary heat exchanger configured to receive a third fluid and which facilitates heat transfer between the third fluid and the first fluid in the primary circuit.

Example 13 is the system of example 1, wherein the heat exchanger includes a thermoelectric heater/cooler thermally coupled to the heat exchanger to heat/cool at least one of the first fluid and the second fluid.

Example 14 is the system of example 1, wherein the heat exchanger includes an auxiliary electric heater configured to heat the second fluid in the heat exchanger.

Example 15 is the system of example 1, wherein the target device includes an oxygenator heat exchanger.

Example 16 is the system of example 15, including a first temperature sensor configured to take temperature measurements of blood and a second temperature sensor configured to take temperature measurements of at least one of the first fluid and the second fluid, wherein the system is configured to maintain a predefined temperature offset between the blood and the at least one of the first fluid and the second fluid.

Example 17 is the system of example 1, wherein the heat exchanger includes one or more auxiliary electric heaters used during thermal disinfection to dry and thermally disinfect the heat exchanger.

Example 18 is the system of example 1, wherein the heat exchanger includes one or more temperature sensors configured to measure a temperature of the heat exchanger in the absence of the second fluid.

Example 19 is the system of example 1, wherein the heat exchanger includes a first module configured to receive the first fluid and a disposable module configured to receive the second fluid.

Example 20 is the system of example 19, wherein the first module includes one or more auxiliary electric heaters to heat at least one of the first fluid and the second fluid.

Example 21 is the system of example 19, wherein the first module includes a temperature sensor configured to measure the temperature of at least one of the first fluid and the second fluid.

Example 22 is the system of example 19, wherein the disposable module includes one or more auxiliary electric heaters to heat at least one of the first fluid and the second fluid.

Example 23 is the system of example 19, wherein the disposable module includes at least one temperature sensor configured to measure a temperature of at least one of the first fluid and the second fluid.

Example 24 is the system of example 19, wherein the first module includes a first plate heat exchanger and the disposable module includes a second plate heat exchanger.

Example 25 is the system of example 1, wherein the heat exchanger includes a plate heat exchanger configured to receive the first fluid and a disposable plate heat exchanger configured to receive the second fluid.

Example 26 is a system including a heater/cooler module including a primary circuit and a heat pump to heat/cool a first fluid in the primary circuit, a heat transfer fluid circuit including a secondary circuit that contains a second fluid and is configured to provide the second fluid to a target device in the secondary circuit to facilitate heat transfer between the second fluid and a target fluid in the target device, and a heat exchanger circuit including at least part of the primary circuit through which the first fluid flows and at least part of the secondary circuit through which the second fluid flows to regulate temperature of the second fluid via the first fluid.

Example 27 is the system of example 26, wherein the primary circuit includes a heat exchanger coil in the heat exchanger and the secondary circuit includes a container that is sealed around the heat exchanger coil.

Example 28 is the system of example 27, wherein the first fluid flows through the heat exchanger coil to facilitate heat transfer between the first fluid and the heat exchanger coil to achieve a first temperature of the heat exchanger coil and the second fluid flows around the heat exchanger coil to facilitate heat transfer between the second fluid and the heat exchanger coil to achieve a second temperature of the second fluid.

Example 29 is the system of example 27, wherein the heat exchanger includes an auxiliary electric heater configured to provide heat to the second fluid.

Example 30 is the system of example 27, wherein the heat exchanger includes at least one temperature sensor configured to provide temperature measurements of the second fluid.

Example 31 is the system of example 26, wherein the heat exchanger includes a heat exchanger structure and the secondary circuit includes a container that is sealed around the heat exchanger structure.

Example 32 is the system of example 31, wherein the first fluid and the heat exchanger structure facilitate heat transfer between the first fluid and the heat exchanger structure to achieve a first temperature of the heat exchanger structure, and the second fluid flows through the container and around the heat exchanger structure in the container to facilitate heat transfer between the heat exchanger structure and the second fluid to achieve a second temperature of the second fluid.

Example 33 is the system of example 31, wherein the heat exchanger comprises an auxiliary electric heater configured to provide heat to the second fluid.

Example 34 is the system of example 31, wherein the heat exchanger comprises a temperature sensor configured to provide temperature measurements of the second fluid.

Example 35 is the system of example 26, wherein the heater/cooler module includes an auxiliary heat exchanger configured to receive a third fluid to facilitate heat transfer between the third fluid and the first fluid in the primary circuit.

Example 36 is the system of example 26, wherein the heat exchanger includes a thermoelectric heater/cooler coupled to the heat exchanger to heat/cool the first fluid in the primary circuit.

Example 37 is the system of example 26, wherein the heat transfer fluid circuit is a single use disposable unit.

Example 38 is a method of heating/cooling a target fluid in a target device via a heater/cooler module including a first fluid in a primary circuit, a pump, a heater/cooler element, and a heat exchanger, the method including pumping the first fluid through the primary circuit and the heat exchanger via the pump, heating/cooling the first fluid in the primary circuit with the heater/cooler element, providing a second fluid in a secondary circuit that is separate from the primary circuit, such that the first fluid and the second fluid are maintained as separate fluids, pumping the second fluid through the secondary circuit and the heat exchanger, facilitating heat transfer in the heat exchanger between the second fluid in the secondary circuit and the first fluid in the primary circuit, and providing the second fluid to the target device to facilitate heat transfer between the second fluid and the target fluid.

Example 39 is the method of example 38, wherein heating/cooling the first fluid comprises heating/cooling the first fluid in the primary circuit with a heat pump.

Example 40 is the method of example 38, wherein heating/cooling the first fluid comprises heating/cooling the first fluid in the primary circuit with an auxiliary heat exchanger in the heater/cooler module, the auxiliary heat exchanger configured to receive a third fluid to facilitate heat transfer between the third fluid and the first fluid in the primary circuit.

Example 41 is the method of example 38, wherein heating/cooling the first fluid comprises heating/cooling the first fluid in the primary circuit with a thermoelectric heater/cooler coupled to the heat exchanger.

Example 42 is the method of example 38, including heating at least one of the first fluid in the heat exchanger and the second fluid in the heat exchanger with one or more auxiliary electric heaters coupled to the heat exchanger.

Example 43 is the method of example 38, wherein facilitating heat transfer between the second fluid in the secondary circuit and the first fluid in the primary circuit includes pumping the first fluid through a heat exchanger coil that is part of the primary circuit and situated in the heat exchanger, and pumping the second fluid through a container that is sealed around the heat exchanger coil, such that the second fluid flows around the heat exchanger coil.

Example 44 is the method of example 38, wherein facilitating heat transfer between the second fluid in the secondary circuit and the first fluid in the primary circuit includes pumping the first fluid through a heat exchanger structure that is part of the primary circuit and situated in the heat exchanger, and pumping the second fluid through a container that is sealed around the heat exchanger structure, such that the second fluid flows around the heat exchanger structure.

Example 45 is the method of example 38, wherein facilitating heat transfer between the second fluid in the secondary circuit and the first fluid in the primary circuit includes pumping the first fluid through a first plate heat exchanger that is part of the primary circuit and situated in the heat exchanger, pumping the second fluid through a second plate heat exchanger that is part of the secondary circuit and the heat transfer fluid circuit, and facilitating heat transfer between the first plate heat exchanger and the second plate heat exchanger to heat/cool the second fluid.

Example 46 is the method of example 38, including regulating a temperature of the target fluid in the target device by measuring a fluid temperature of at least one of the first fluid and the second fluid.

Example 47 is the method of example 38, including maintaining a predefined temperature offset between the target fluid in the target device and at least one of the first fluid and the second fluid.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
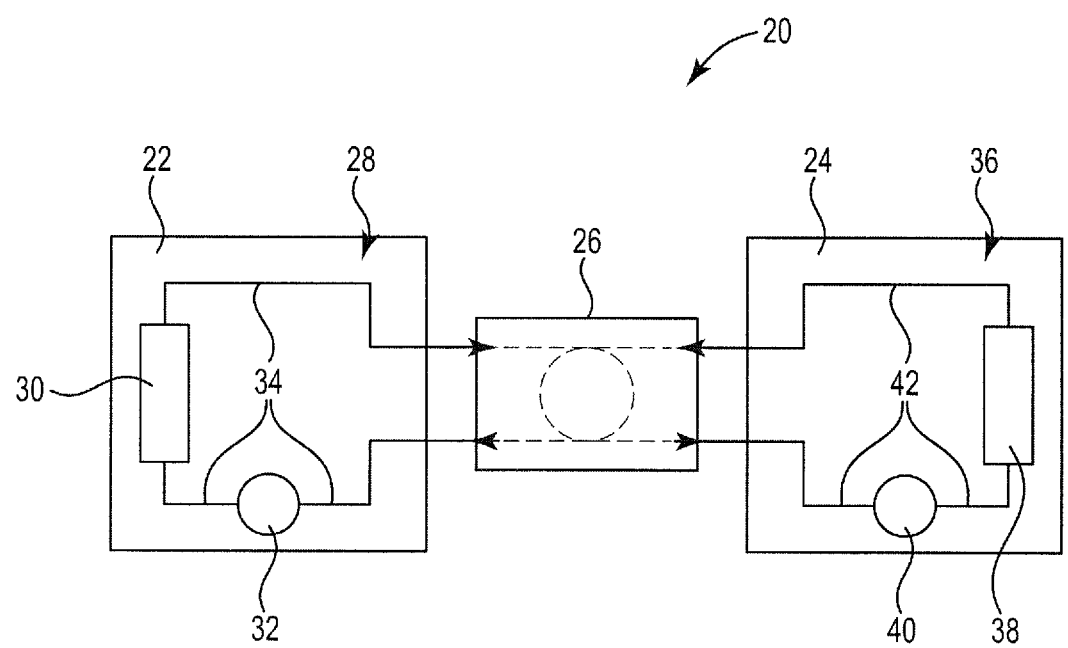
FIG. 1 is a diagram illustrating a modular heating/cooling system, according to embodiments of the disclosure.

While the disclosure is amendable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

FIG. 1 is a diagram illustrating a modular heating/cooling system 20, according to embodiments of the disclosure. The modular heating/cooling system 20 includes a heater/cooler module 22, a heat transfer fluid circuit 24, and a heat exchanger 26. The different parts of the system 20, including the heater/cooler module 22, the heat transfer fluid circuit 24, and/or the heat exchanger 26, can be "stacked" or coupled to other similar parts to provide an increase in the heating/cooling capability of the system 20 and/or to increase the number of heating/cooling channels. For example, multiple heater/cooler modules 22 and/or multiple heat transfer fluid circuits 24 and/or multiple heat exchangers 26 can be "stacked" to provide an increase in heating/cooling capability and/or an increase in heating/cooling channels. Also, having multiple similar parts provides redundancy in case of failure of any of the parts, and modularity allows the system 20 to be customized to fit different power consumption needs and to provide optimized heating/cooling capabilities, as required for different applications.

In most applications, system 20 includes one of each of the heater/cooler module 22, the heat transfer fluid circuit 24, and/or the heat exchanger 26. In these embodiments, the system 20 consumes 500-600 watts, which makes the system 20 compatible with portable applications, such as ambulance, aircraft, and helicopter applications. Also, low power consumption makes the system 20 compatible with battery operation and with the use of uninterruptible power supplies (UPS's). In addition, low power consumption makes the system 20 compatible with electrical systems in multiple countries, where the system 20 can be plugged into one power outlet without overpowering the single outlet. Thus, the system 20 can be used in Europe where one electrical power outlet may supply up to 3.5 kilowatts, and in the United States where one power outlet may supply 1.8 kilowatts, and in Japan where one power outlet may supply only up to 1.5 kilowatts.

Also, the modular heating/cooling system 20 has size advantages making it compatible with applications in small areas, such as placing the system 20 or components of the system 20 near a heart lung machine (HLM). In some embodiments, the system 20 takes up an area or volume of only 0.5×0.5×0.5 meters. This, along with the low power consumption, makes the system 20 available for the portable applications.

The system 20 can be used in different heating/cooling applications in the medical field. These medical field applications include heating/cooling of the blood in an oxygenator, heating/cooling of a drug or drugs in cardioplegia, heating/cooling of clothing or other items such as blankets, hyperthermia and hypothermia procedures, and the heating/cooling of fluids in organ perfusion. In addition, the modular heating/cooling system 20 can be used in cardiopulmonary bypass (CPB) and extracorporeal membrane oxygenation (ECMO), such as in an intensive care unit (ICU).

The heater/cooler module 22 includes a primary circuit 28 including a heater/cooler element 30 fluidically coupled to a primary circuit pump 32 via primary circuit tubing 34. The primary circuit 28 includes a first fluid in the primary circuit 28 and the primary circuit tubing 34 is fluidically coupled to the heat exchanger 26. In some embodiments, the heater/cooler element 30 includes a heat pump. In some embodiments, the primary circuit pump 32 includes a pump of a HLM and/or a standalone pump. In some embodiments, the first fluid includes water. In some embodiments, the primary circuit 28 is a permanent part of the heater/cooler module 22.

In some embodiments, the primary circuit 28 is a closed circuit containing the first fluid. In some embodiments, the primary circuit 28 is a hermetically sealed closed circuit containing the first fluid. In embodiments where the primary circuit 28 is a closed circuit, the system 20 prevents contamination of the OR due to open air tanks holding the first fluid. Also, these embodiments eliminate the need for disinfecting the primary circuit 28.

The heat transfer fluid circuit 24 includes a secondary circuit 36 including a target device 38 fluidically coupled to a secondary circuit pump 40 via secondary circuit tubing 42. The secondary circuit 36 includes a second fluid in the secondary circuit 36 and the secondary circuit tubing 42 is fluidically coupled to the heat exchanger 26. In some embodiments, the heat transfer fluid circuit 24 is a single use disposable circuit. In some embodiments, the secondary circuit pump 40 is part of the heater/cooler module 22. In some embodiments, the secondary circuit pump 36 includes a pump of a HLM and/or a standalone pump. In some embodiments, the second fluid includes water. In some embodiments, the secondary circuit 36 is disposable.

In some embodiments, the secondary circuit 36 is a closed circuit containing the second fluid. In some embodiments, the secondary circuit 36 is a hermetically sealed closed circuit containing the second fluid. In embodiments where the secondary circuit 36 is a closed circuit, the system 20 prevents contamination of the OR due to open air tanks holding the second fluid. Also, these embodiments eliminate the need for disinfecting the secondary circuit 36.

In some embodiments, the heat transfer fluid circuit 24 is a reusable circuit that is cleaned and disinfected after one or more uses. In other embodiments, at least part of the secondary circuit 36 is part of the heater/cooler module 22 and non-disposable, such that the at least part of the secondary circuit 36 is cleaned and disinfected after one or more uses. In disinfecting, the secondary circuit 36 is emptied of any residual second fluid and hot disinfected at a temperature, such as 95 C, for a specified time to sterilize the circuit, including the prevention of bacterial growth.

The primary circuit pump 32 in the heater/cooler module 22 pumps the first fluid around and through the primary circuit 28, including through the primary circuit tubing 34 and the heat exchanger 26. The heater/cooler element 30 is controlled to heat/cool the first fluid. The secondary circuit pump 40, which in some embodiments is part of the heat transfer fluid circuit 24 and in some embodiments is part of the heater/cooler module 22, pumps the second fluid around and through the secondary circuit tubing 42, the target device 38, and the heat exchanger 26. The secondary circuit 36 provides the second fluid to the target device 38 to heat/cool the target device 38. The primary circuit 28 and the secondary circuit 36 are separate circuits, such that the first fluid and the second fluid remain separated in the system 20.

The heat exchanger 26 includes at least part of the primary circuit 28 through which the first fluid flows and at least part of the secondary circuit 36 through which the second fluid flows to facilitate heat transfer between the first fluid and the second fluid. The temperature of the second fluid is regulated by the temperature of the first fluid. In some embodiments, the target device 38 includes a target fluid and the second fluid flows through the target device 38 to facilitate heat transfer between the second fluid and the target fluid.

Figure 2:
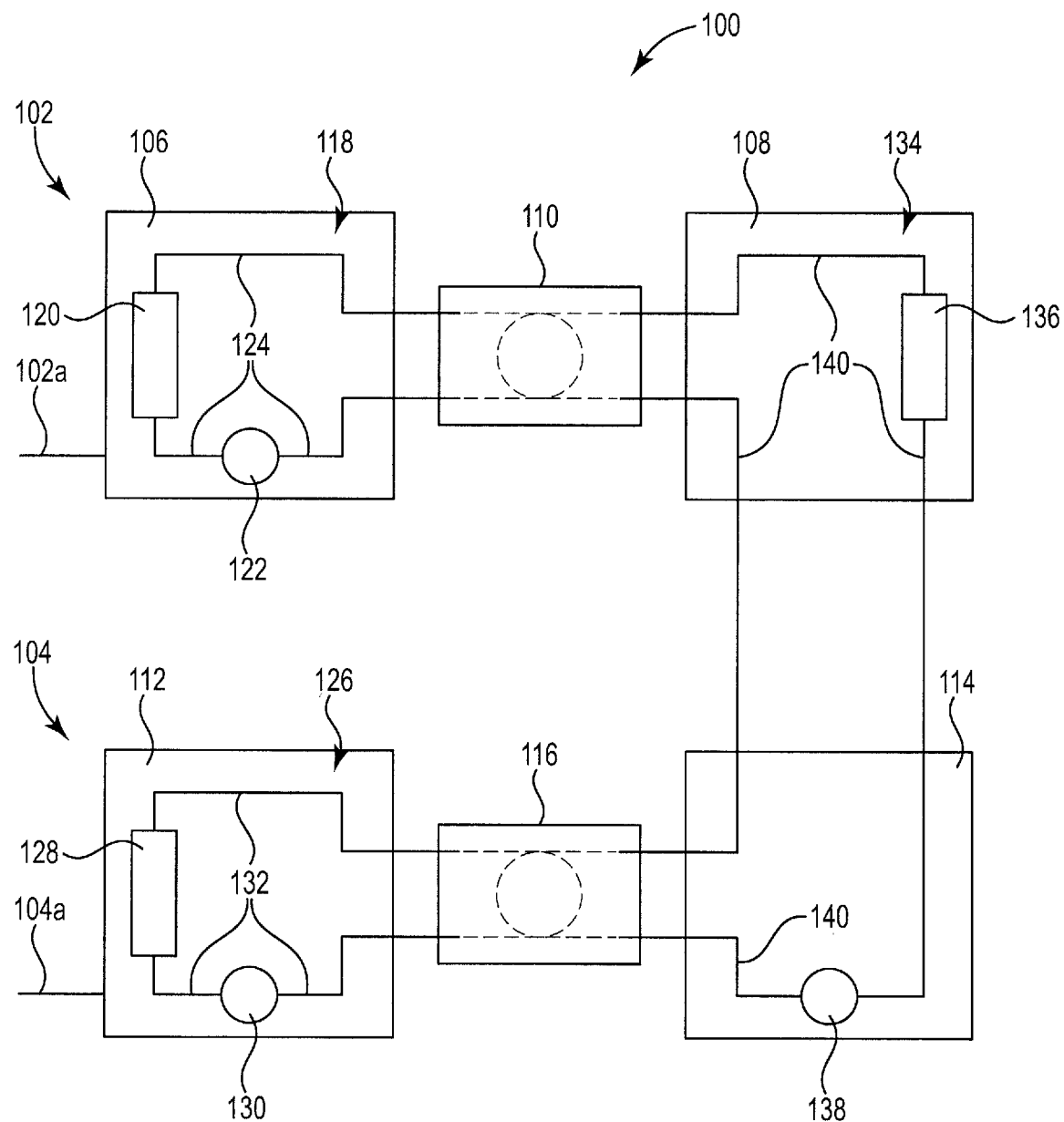
FIG. 2 is a diagram illustrating a stacked modular heating/cooling system including a first modular heating/cooling system and a second modular heating/cooling system, according to embodiments of the disclosure.

FIG. 2 is a diagram illustrating a stacked modular heating/cooling system 100 including a first modular heating/cooling system 102 and a second modular heating/cooling system 104, according to embodiments of the disclosure. The first modular heating/cooling system 102 includes a heater/cooler module 106, a heat transfer fluid circuit 108, and a heat exchanger 110. The second modular heating/cooling system 104 includes a heater/cooler module 112, a heat transfer fluid circuit 114, and a heat exchanger 116. The first modular heating/cooling system 102 includes an electrical power connection 102a for powering the first modular heating/cooling system 102 and the second modular heating/cooling system 104 includes an electrical power connection 104a for powering the second modular heating/cooling system 104. In some embodiments, one or more of the heater/cooler modules 106 and 112 is similar to the heater/cooler module 22. In some embodiments, one or more of the heat transfer fluid circuits 108 and 114 is similar to the heat transfer fluid circuit 24. In some embodiments, one or more of the heat exchangers 110 and 116 is similar to the heat exchanger 26. In other embodiments, the stacked modular heating/cooling system 100 includes a different number of heater/cooler modules, heat transfer fluid circuits, and/or heat exchangers to provide an increase in heating/cooling capability and/or an increase in heating/cooling channels.

In some embodiments, each of the first and second modular heating/cooling systems 102 and 104 consumes 500-600 watts, such that the stacked modular heating/cooling system 100 consumes 1000-1200 watts. In these embodiments, the stacked modular heating/cooling system 100 can be powered via one electrical power outlet in Europe where one electrical power outlet may supply up to 3.5 kilowatts, and in the United States where one power outlet may supply 1.8 kilowatts, and in Japan where one power outlet may supply up to 1.5 kilowatts. Alternatively, each of the first and second modular heating/cooling systems 102 and 104 can be plugged into separate outlets.

As with system 20 of FIG. 1, the system 100 can be used in different heating/cooling applications in the medical field, including heating/cooling of the blood in an oxygenator, heating/cooling of a drug or drugs in cardioplegia, heating/cooling of clothing or other items such as blankets, hyperthermia and hypothermia procedures, and the heating/cooling of fluids in organ perfusion. Also, the system 100 can be used in CPB and ECMO applications, such as in an ICU.

Heater/cooler module 106 includes a primary circuit 118 including a heater/cooler element 120 fluidically coupled to a primary circuit pump 122 via primary circuit tubing 124. The primary circuit 118 contains a first fluid and the primary circuit tubing 124 is fluidically coupled to heat exchanger 110. Heater/cooler module 112 includes a primary circuit 126 including a heater/cooler element 128 fluidically coupled to a primary circuit pump 130 via primary circuit tubing 132. The primary circuit 126 contains another first fluid and the primary circuit tubing 132 is fluidically coupled to heat exchanger 116. In some embodiments, one or more of the heater/cooler elements 120 and 128 includes a heat pump. In some embodiments, one or more of the primary circuit pumps 122 and 130 includes a pump of a HLM and/or a standalone pump. In some embodiments, one or more of the first fluids includes water. In some embodiments, one or more of the primary circuits 118 and 126 is a permanent part of its corresponding heater/cooler module 106 and 112.

In some embodiments, one or more of the primary circuits 118 and 126 is a closed circuit containing its corresponding first fluid. In some embodiments, one or more of the primary circuits 118 and 126 is a hermetically sealed closed circuit containing its corresponding first fluid. In embodiments, where one or more of the primary circuits 118 and 126 is a closed circuit, the closed circuit prevents contamination of the OR due to open air tanks holding a fluid. Also, these embodiments eliminate the need for disinfecting the closed circuit primary circuits 118 and 126.

The heat transfer fluid circuits 108 and 114 include a secondary circuit 134 that includes a target device 136 fluidically coupled to a secondary circuit pump 138 via secondary circuit tubing 140. The secondary circuit 134 contains a second fluid. The secondary circuit tubing 140 is fluidically coupled to each of the heat exchangers 110 and 116, and the secondary circuit tubing 140 fluidically couples heat exchanger 110 to heat exchanger 116. In some embodiments, each of the heat transfer fluid circuits 108 and 114 is a single use disposable circuit. In some embodiments, the secondary circuit pump 138 is part of at least one of the first and second modular heating/cooling systems 102 and 104. In some embodiments, the secondary circuit pump 138 includes a pump of a HLM and/or a standalone pump. In some embodiments, the second fluid includes water. In some embodiments, the secondary circuit 134 is disposable.

In some embodiments, the secondary circuit 134 is a closed circuit containing the second fluid. In some embodiments, the secondary circuit 134 is a hermetically sealed closed circuit containing the second fluid. In embodiments, where the secondary circuit 134 is a closed circuit, the system 20 prevents contamination of the OR due to open air tanks holding a fluid. Also, these embodiments eliminate the need for disinfecting the secondary circuit 134.

In some embodiments, one or more of the heat transfer fluid circuits 108 and 114 are reusable circuits that can be cleaned and disinfected after one or more uses. In other embodiments, at least part of the secondary circuit 134 is part of one of the heater/cooler modules 106 and 112 and non-disposable, such that the at least part of the secondary circuit 134 is cleaned and disinfected after one or more uses. In disinfecting, the secondary circuit 134 is emptied of any residual second fluid and hot disinfected at a temperature, such as 95 C, for a specified time to sterilize the circuit, which includes preventing bacterial growth.

The primary circuit pump 122 in the heater/cooler module 106 pumps the first fluid around and through the primary circuit 118, including through the primary circuit tubing 124 and the heat exchanger 110. The heater/cooler element 120 is controlled to heat/cool the first fluid in the primary circuit 118.

The primary circuit pump 130 in the heater/cooler module 112 pumps the first fluid around and through the primary circuit 126, including through the primary circuit tubing 132 and the heat exchanger 116. The heater/cooler element 128 is controlled to heat/cool the first fluid in the primary circuit 126.

The secondary circuit pump 138, which in some embodiments is part of at least one of the heat transfer fluid circuits 108 and 114 and in some embodiments is part of at least one of the first and second modular heating/cooling systems 102 and 104, pumps the second fluid around and through the secondary circuit tubing 140, the target device 136, and the heat exchangers 110 and 116. The secondary circuit 134 provides the second fluid to the target device 136 to heat/cool the target device 136. The primary circuits 118 and 126 are separate circuits such that the first fluids in each remain separated. Also, the primary circuits 118 and 126 and the secondary circuit 134 are separate circuits, such that each of the first fluids and the second fluid remain separated in the system 100.

The heat exchangers 110 and 116 include at least part of the corresponding primary circuits 118 and 126 through which the first fluids flow and at least part of the secondary circuit 134 through which the second fluid flows to facilitate heat transfer between the first fluids and the second fluid. The temperature of the second fluid is regulated by the temperature of the first fluids. In some embodiments, the target device 136 includes a target fluid and the second fluid flows through the target device 136 to facilitate heat transfer between the second fluid and the target fluid.

Having multiple heater/cooler modules 106 and 112 and multiple heat exchangers 110 and 116 enable the system 100 to heat/cool the target device 136 more quickly and/or to higher/lower temperatures.

Figure 3A:
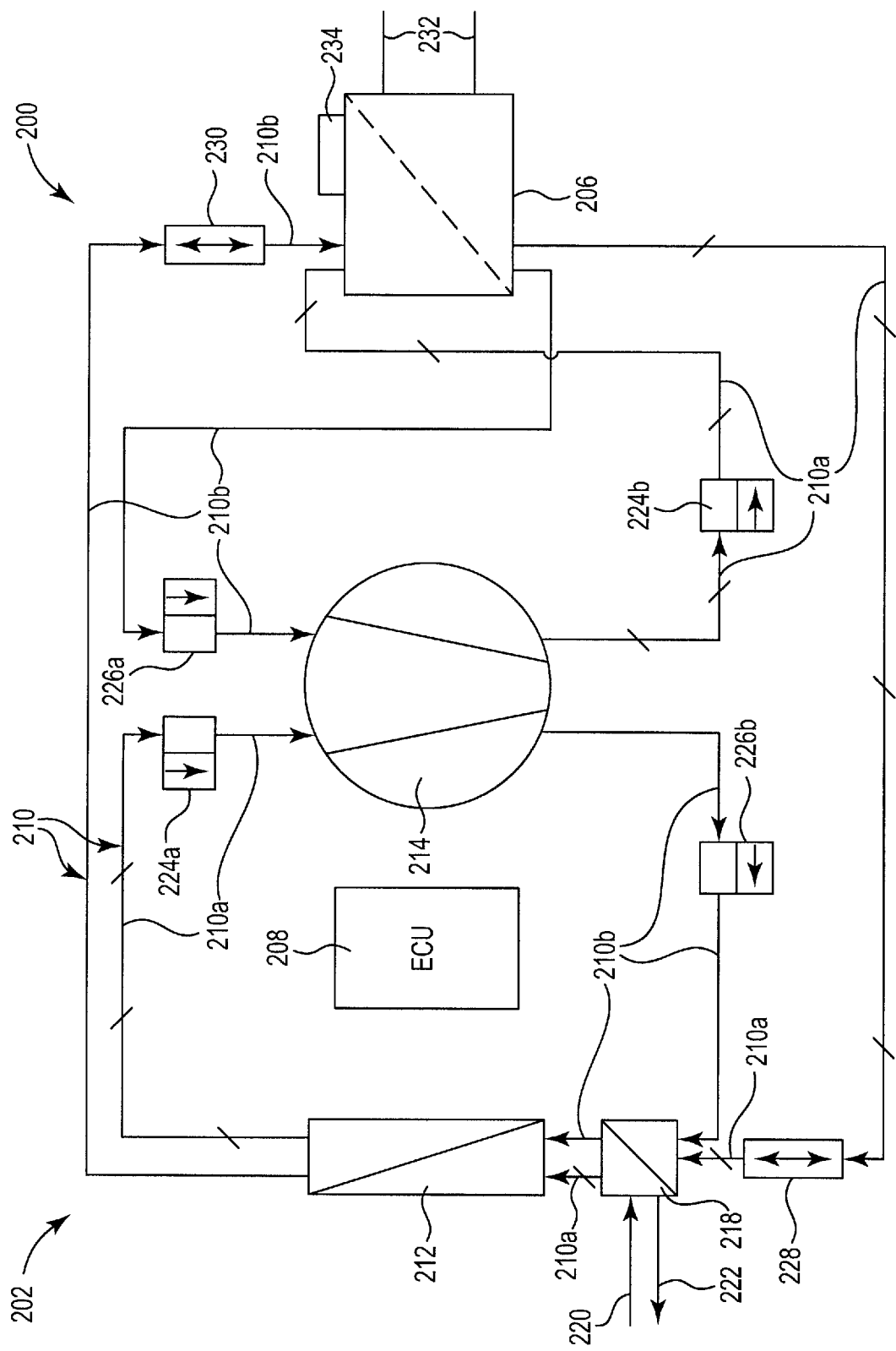
FIG. 3A is a diagram illustrating the heater/cooler module and the heat exchanger, according to embodiments of the disclosure.
Figure 3B:
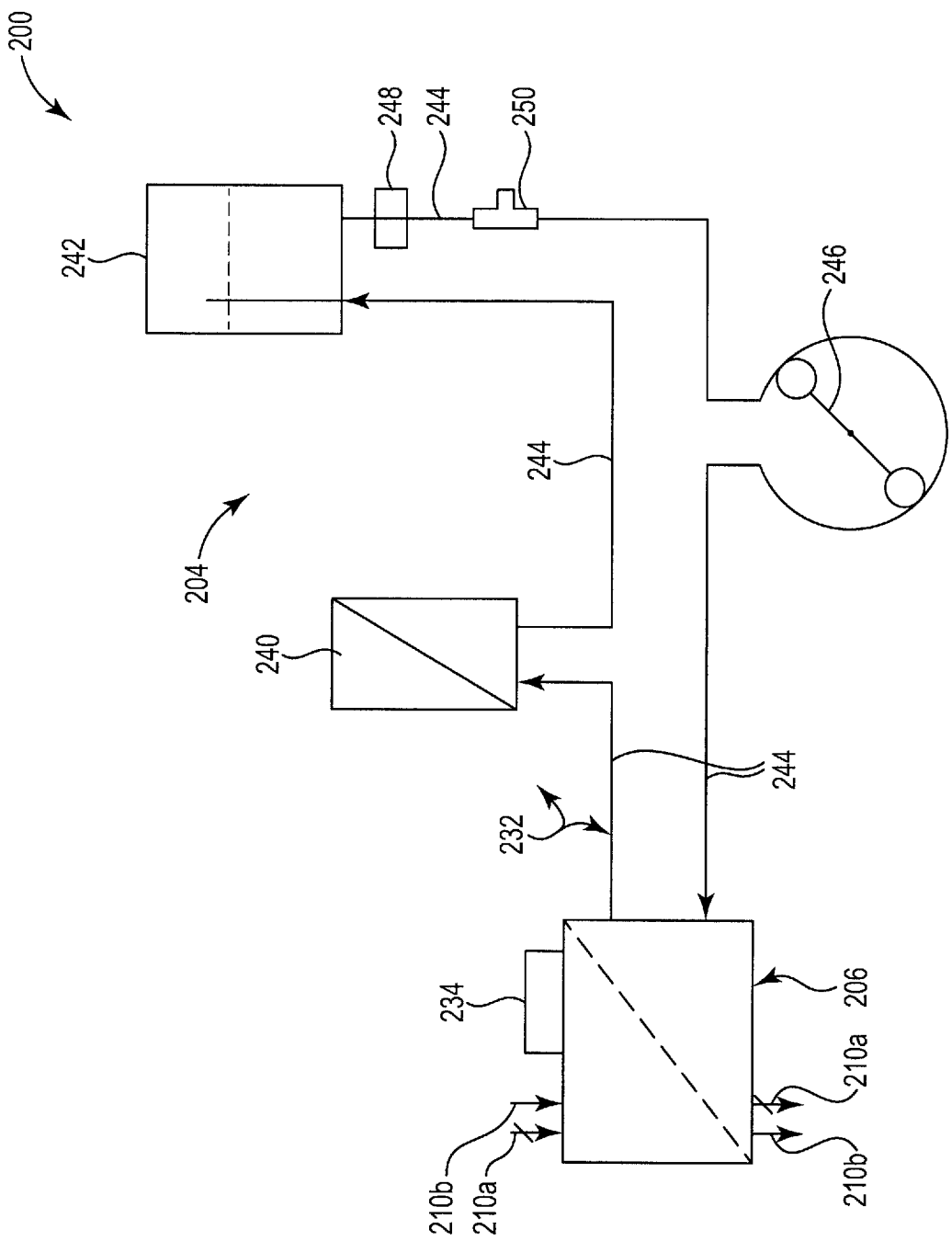
FIG. 3B is a diagram illustrating the heat transfer fluid circuit and the heat exchanger, according to embodiments of the disclosure.

FIGS. 3A and 3B are diagrams illustrating another modular heating/cooling system 200, according to embodiments of the disclosure. The modular heating/cooling system 200 is similar to system 20 of FIG. 1. The system 200 includes a heater/cooler module 202, a heat transfer fluid circuit 204, and a heat exchanger 206.

Similar to system 20, the different parts of system 200, including the heater/cooler module 202, the heat transfer fluid circuit 204, and/or the heat exchanger 206, can be "stacked" or coupled to other similar parts to provide an increase in the heating/cooling capability of the system 200 and/or to increase the number of heating/cooling channels.

In most applications system 200 includes one of each of the heater/cooler module 202, the heat transfer fluid circuit 204, and the heat exchanger 206, and the system 200 consumes 500-600 watts. This makes system 200 compatible with portable applications, such as ambulance, aircraft, and helicopter applications. Also, low power consumption makes the system 200 compatible with battery operation and with the use of uninterruptible power supplies (UPS's). In addition, low power consumption makes the system 200 compatible with electrical systems in multiple countries, where the system 200 can be plugged into one power outlet without overpowering the single outlet. Thus, the system 200 can be used in Europe where one electrical power outlet may supply up to 3.5 kilowatts, and in the United States where one power outlet may supply 1.8 kilowatts, and in Japan where one power outlet may supply up to 1.5 kilowatts.

The modular heating/cooling system 200 also has size advantages making it compatible with applications in small areas, such as placing the system 200 or components of the system 200 near a heart lung machine (HLM). In some embodiments, the system 200 takes up an area or volume of only 0.5×0.5×0.5 meters. This, along with low power consumption, makes the system 200 available for the portable applications.

The system 200 can be used in different heating/cooling applications in the medical field, such as heating/cooling of the blood in an oxygenator, heating/cooling of a drug or drugs in cardioplegia, heating/cooling of clothing or other items such as blankets, hyperthermia and hypothermia procedures, and the heating/cooling of fluids in organ perfusion. In addition, the modular heating/cooling system 200 can be used in cardiopulmonary bypass (CPB) and extracorporeal membrane oxygenation (ECMO), such as in an intensive care unit (ICU).

FIG. 3A is a diagram illustrating the heater/cooler module 202 and the heat exchanger 206, according to embodiments of the disclosure. In some embodiments, the heater/cooler module 202 is similar to one or more of the heater/cooler modules 22, 106, and 112. In some embodiments, the heat exchanger 206 is similar to the heat exchanger 26.

The heater/cooler module 202 includes an electronic control unit 208 and a primary circuit 210 for heating and cooling a first fluid in the primary circuit 210. The electronic control unit 208 can be one or more of a controller, a processor, a micro-controller, a micro-processor, and a computer. Also, the electronic control unit 208 can include memory, a user interface having input and output portions, such as a touch screen display, and executable code stored in memory that the electronic control unit 208 executes to control the components of the heater/cooler module 202. The primary circuit 210 includes heating circuit tubing 210a, indicated by slashes on the tubing 210a, in a heating circuit path for heating the first fluid, and cooling circuit tubing 210b, indicated with non-slashed tubing 210b, in a cooling circuit path for cooling the first fluid. In some embodiments, the first fluid includes water. In some embodiments, the primary circuit 210 is a permanent part of the heater/cooler module 202.

In some embodiments, the primary circuit 210, including the heating circuit path and the cooling circuit path, is a closed circuit containing the first fluid. In some embodiments, the primary circuit 210, including the heating circuit path and the cooling circuit path, is a hermetically sealed closed circuit containing the first fluid. In embodiments where the primary circuit 210 is a closed circuit, the system 200 prevents contamination of the OR due to open air tanks holding the first fluid. Also, these embodiments eliminate the need for disinfecting the primary circuit 210.

The primary circuit 210 includes a heater/cooler element 212, a primary circuit pump 214, part of the heat exchanger 206 and, optionally, an auxiliary heat exchanger 218. In some embodiments, the heater/cooler element 212 includes a heat pump. In some embodiments, the primary circuit pump 214 includes a pump of a HLM and/or a standalone pump. In some embodiments, the auxiliary heat exchanger 218 receives a heat exchanger fluid at 220 and transmits the heat exchanger fluid at 222. The heat exchanger fluid is pumped through the auxiliary heat exchanger 218 to facilitate heat transfer between the heat exchanger fluid and the first fluid.

The primary circuit path 210 also includes heating circuit valves 224a and 224b and cooling circuit valves 226a and 226b. In addition, the primary circuit path 210 includes a heating circuit expansion valve 228 and a cooling circuit expansion valve 230. The electronic control unit 208 is electrically coupled to the heater/cooler element 212, the primary circuit pump 214, the heat exchanger 206, the auxiliary heat exchanger 218, the heating circuit valves 224a and 224b, the cooling circuit valves 226a and 226b, the heating circuit expansion valve 228, and the cooling circuit expansion valve 230 to control operation of the heater/cooler module 202.

In the heating circuit path, the heating circuit tubing 210a fluidically couples the following components together: the heater/cooler element 212 is fluidically coupled to the heating circuit valve 224a that is fluidically coupled to the primary circuit pump 214 that is fluidically coupled to the heating circuit valve 224b that is fluidically coupled to the heat exchanger 206 that is fluidically coupled to the heating circuit expansion valve 228 that is fluidically coupled to the auxiliary heat exchanger 218 that is fluidically coupled to the heater/cooler element 212.

In the cooling circuit path, the cooling circuit tubing 210b fluidically couples the following components together: the heater/cooler element 212 is fluidically coupled to the cooling circuit expansion valve 230 that is fluidically coupled to the heat exchanger 206 that is fluidically coupled to the cooling circuit valve 226a that is fluidically coupled to the primary circuit pump 214 that is fluidically coupled to the cooling circuit valve 226b that is fluidically coupled to the auxiliary heat exchanger 218 that is fluidically coupled to the heater/cooler element 212.

In heating the first fluid, the primary circuit pump 214 pumps the first fluid through the heating circuit path including the heating circuit valve 224b to the heat exchanger 206 to the heating circuit expansion valve 228 to the auxiliary heat exchanger 218 to the heater/cooler element 212 to the heating circuit valve 224a and back to the primary circuit pump 214. The primary circuit pump 214 and the heater/cooler element 212 are controlled by the electronic control unit 208 to heat the first fluid. Also, optionally, the auxiliary heat exchanger 218 is controlled, such as by the electronic control unit 208, to heat the first fluid.

In cooling the first fluid, the primary circuit pump 214 pumps the first fluid through the cooling circuit path including the cooling circuit valve 226b to the auxiliary heat exchanger 218 to the heater/cooler element 212 to the cooling circuit expansion valve 230 to the heat exchanger 206 to the cooling circuit valve 226a and back to the primary circuit pump 214. The primary circuit pump 214 and the heater/cooler element 212 are controlled by the electronic control unit 208 to cool the first fluid. Also, optionally, the auxiliary heat exchanger 218 is controlled, such as by the electronic control unit 208, to cool the first fluid.

The heat exchanger 206 includes at least part of the primary circuit 210 through which the first fluid flows and at least part of a secondary circuit 232 through which a second fluid flows to facilitate heat transfer between the first fluid and the second fluid. The temperature of the second fluid is regulated by the temperature of the first fluid. In some embodiments, the heat exchanger 206 includes a thermoelectric heater/cooler 234 thermally coupled to the heat exchanger 206 to heat and/or cool at least one of the first fluid and the second fluid. In some embodiments, the thermoelectric heater/cooler 234 is controlled by the electronic control unit 208. In some embodiments, a target device includes a target fluid and the second fluid flows through the target device to facilitate heat transfer between the second fluid and the target fluid.

In some embodiments, the heat exchanger 206 includes one or more auxiliary electric heaters configured to heat the first fluid in the heat exchanger 206. In some embodiments, the heat exchanger 206 includes one or more auxiliary electric heaters configured to heat the second fluid in the heat exchanger 206. In some embodiments, the heat exchanger 206 includes one or more auxiliary electric heaters configured to be used during thermal disinfection to dry and thermally disinfect the heat exchanger 206. In some embodiments, one or more auxiliary electric heaters in the heat exchanger 206 are controlled by the electronic control unit 208.

FIG. 3B is a diagram illustrating the heat transfer fluid circuit 204 and the heat exchanger 206, according to embodiments of the disclosure. In some embodiments, the heat transfer fluid circuit 204 is similar to the heat transfer fluid circuit 24.

The heat transfer fluid circuit 204 includes the secondary circuit 232 including a target device 240 fluidically coupled to a second fluid reservoir 242 via secondary circuit tubing 244. The second fluid is in the secondary circuit 232 and the secondary circuit tubing 244 is fluidically coupled to the heat exchanger 206. A secondary circuit pump 246 pumps the second fluid around the secondary circuit 232 and through the secondary circuit tubing 244 and the heat exchanger 206. The secondary circuit 232 also includes a clamp 248 for preventing/allowing fluid flow and/or a vent 250 for draining the secondary circuit tubing 244. In some embodiments, the secondary circuit pump 246 is part of the heat transfer fluid circuit 204. In some embodiments, the secondary circuit pump 246 is part of the heater/cooler module 202. In some embodiments, the target device 240 includes a heat exchanger and a target device fluid, such that the heat exchanger facilitates heat transfer between the second fluid and the target device fluid.

In some embodiments, the target device 240 is an oxygenator including a heat exchanger and blood as the target device fluid, such that the heat exchanger facilitates heat transfer between the second fluid and the blood to maintain a specified temperature or temperature range of the blood. In some embodiments, the target device 240 includes a first temperature sensor for sensing the temperature of the blood and the system 200 includes a second temperature sensing device for sensing the temperature of the first fluid. In some embodiments, the target device 240 includes a first temperature sensor for sensing the temperature of the blood and the system 200 includes a second temperature sensing device for sensing the temperature of the second fluid. In some embodiments, the target device 240 includes a first temperature sensor for sensing the temperature of the blood and the system 200 includes a second temperature sensing device for sensing the temperature of the first fluid and a third temperature sensing device for sensing the temperature of the second fluid. In some embodiments, the first, second, and/or third temperature sensing devices are electrically coupled to the electronic control unit 208. In some embodiments, the system 200 is configured to indicate if the temperature difference between the blood and at least one of the first fluid and the second fluid is greater than 10 degrees centigrade. In some embodiments, the system 200 is configured to maintain a predefined temperature offset between the blood and at least one of the first fluid and the second fluid.

In some embodiments, the heat transfer fluid circuit 204, including the secondary circuit pump 246, is a single use disposable circuit. In some embodiments, the heat transfer fluid circuit 204, not including the secondary circuit pump 246, is a single use disposable circuit. In some embodiments, the secondary circuit 232, including the secondary circuit pump 246, is disposable. In some embodiments, the secondary circuit 232, not including the secondary circuit pump 246, is disposable. In some embodiments, the second fluid includes water. In some embodiments, the secondary circuit pump 246 includes a pump of a HLM and/or a standalone pump. In some embodiments, the secondary circuit pump 246 is part of the heat transfer fluid circuit 204. In some embodiments, the secondary circuit pump 246 is part of the heater/cooler module 202.

In some embodiments, the second fluid reservoir 242 is closed. In some embodiments, the second fluid reservoir 242 is a hermetically sealed, closed container. In some embodiments, the secondary circuit 232 is a closed circuit containing the second fluid. In some embodiments, the secondary circuit 232 is a hermetically sealed closed circuit containing the second fluid. In embodiments where the secondary circuit 232 is a closed circuit, the system 200 prevents contamination of the OR due to open air tanks holding the second fluid. Also, these embodiments eliminate the need for disinfecting the secondary circuit 232.

In some embodiments, the heat transfer fluid circuit 204 is a reusable circuit that is cleaned and disinfected after one or more uses. In other embodiments, at least part of the secondary circuit 204 is part of the heater/cooler module 202 and non-disposable, such that the at least part of the secondary circuit 232 is cleaned and disinfected after one or more uses. In disinfecting, the secondary circuit 232 is emptied of any residual second fluid and hot disinfected at a temperature, such as 95 C, for a specified time to sterilize the circuit, including the prevention of bacterial growth.

The secondary circuit pump 246 pumps the second fluid around and through the secondary circuit tubing 244, the heat exchanger 206, the target device 240, and into the second fluid reservoir 242 and back to the secondary circuit pump 246. The secondary circuit 232 provides the second fluid to the target device 240 to heat/cool the target device 240. The primary circuit 210 and the secondary circuit 232 are separate circuits, such that the first fluid and the second fluid remain separated in the system 200.

The heat exchanger 206 includes at least part of the primary circuit 210 through which the first fluid flows and at least part of the secondary circuit 232 through which the second fluid flows to facilitate heat transfer between the first fluid and the second fluid.

Figures 4A, 4B:
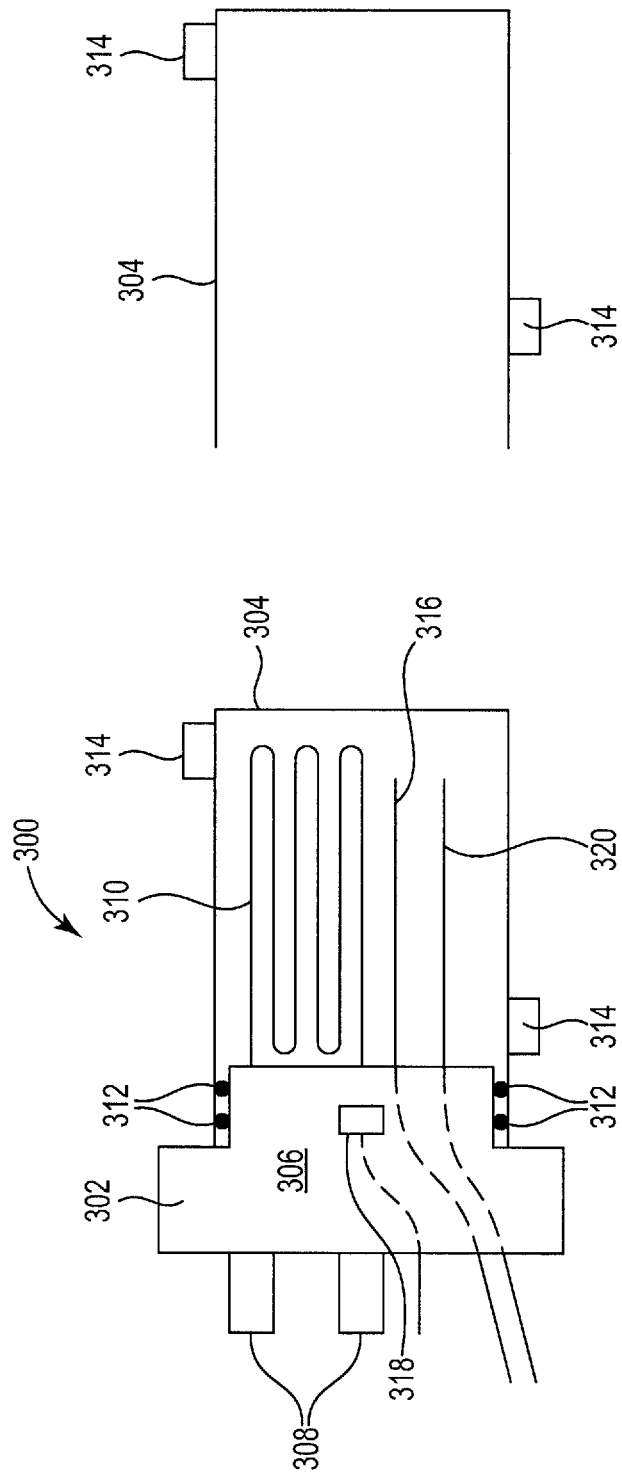
FIG. 4A is a diagram illustrating a heat exchanger, according to embodiments of the disclosure.
FIG. 4B is a diagram illustrating the second module removed from the first module, according to embodiments of the disclosure.

FIG. 4A is a diagram illustrating a heat exchanger 300, according to embodiments of the disclosure. The heat exchanger 300 includes a first module 302 and a second module 304. In some embodiments, the first module 302 is part of the primary circuit of the corresponding heater/cooler module, such that the first module 302 is a primary circuit module. In some embodiments, the second module 304 is part of the secondary circuit of the corresponding heat transfer fluid circuit, such that the second module 304 is a secondary circuit module.

The first module 302 includes a base portion 306 including fluidic connections 308 for fluidically connecting the primary circuit of the corresponding heater/cooler module to the heat exchanger 300. The fluidic connections 308 fluidically communicate a first fluid to coil 310 through which the first fluid flows to achieve a first temperature of the heat exchanger coil 310. The base portion 306 further includes o-rings 312 or other means for securing/sealing the second module 304 to the first module 302 in a fluid-proof or fluid-tight connection that prevents leakage of fluid.

FIG. 4B is a diagram illustrating the second module 304 removed from the first module 302, according to embodiments of the disclosure. The second module 304 includes fluidic connections 314 for fluidically connecting the secondary circuit of the corresponding heat transfer fluid circuit to the second module 304. The fluidic connections 314 fluidically communicate the second fluid through the second module 304 and around the outside of the coil 310 to facilitate heat transfer between the first fluid and the coil 310 with the second fluid to achieve a second temperature of the second fluid. The second module 304 is secured to the first module 302 over the o-rings 312 or other means for securing/sealing the second module 304 to the first module 302 to provide the fluid-tight fit that prevents leakage of the second fluid from the second module 304. In some embodiments, the second module 304 is a disposable module.

In some embodiments, the first module 302 includes an auxiliary electric heater 316 that is controlled to heat the second fluid. In some embodiments, the auxiliary electric heater 316 is used during thermal disinfection to dry and thermally disinfect the heat exchanger 300. In some embodiments, the auxiliary electric heater 316 is electrically coupled to and controlled by the electronic control unit 208. In some embodiments, the heat exchanger 300, such as the base portion 306 of the heat exchanger 300, includes an auxiliary heater, such as an auxiliary electric heater, for heating the first fluid. In some embodiments, the heat exchanger 300 includes one or more auxiliary heaters, such as electric heaters or other suitable types of heaters. In some embodiments, the second module 304 includes one or more auxiliary heaters, such as auxiliary electric heaters, controlled to heat the second fluid.

In some embodiments, the first module 302 includes a temperature sensor 318 to measure a temperature of the heat exchanger 300, such as a temperature of the base portion 306, in the absence of the second fluid in the second module 304. In some embodiments, the temperature sensor 318 is electrically coupled to and read by the electronic control unit 208. In some embodiments, the heat exchanger 300 includes more than one temperature sensor for measuring the temperature of the heat exchanger 300.

In some embodiments, the first module 302 includes a temperature sensor 320 to measure a temperature of the second fluid in the second module 304. In some embodiments, the temperature sensor 320 is electrically coupled to and read by the electronic control unit 208. In some embodiments, the heat exchanger 300 includes more than one temperature sensor for measuring the temperature of at least one of the first fluid and the second fluid. In some embodiments, the second module 304 includes a temperature sensor to measure a temperature of the second fluid in the second module 304.

Figure 5:
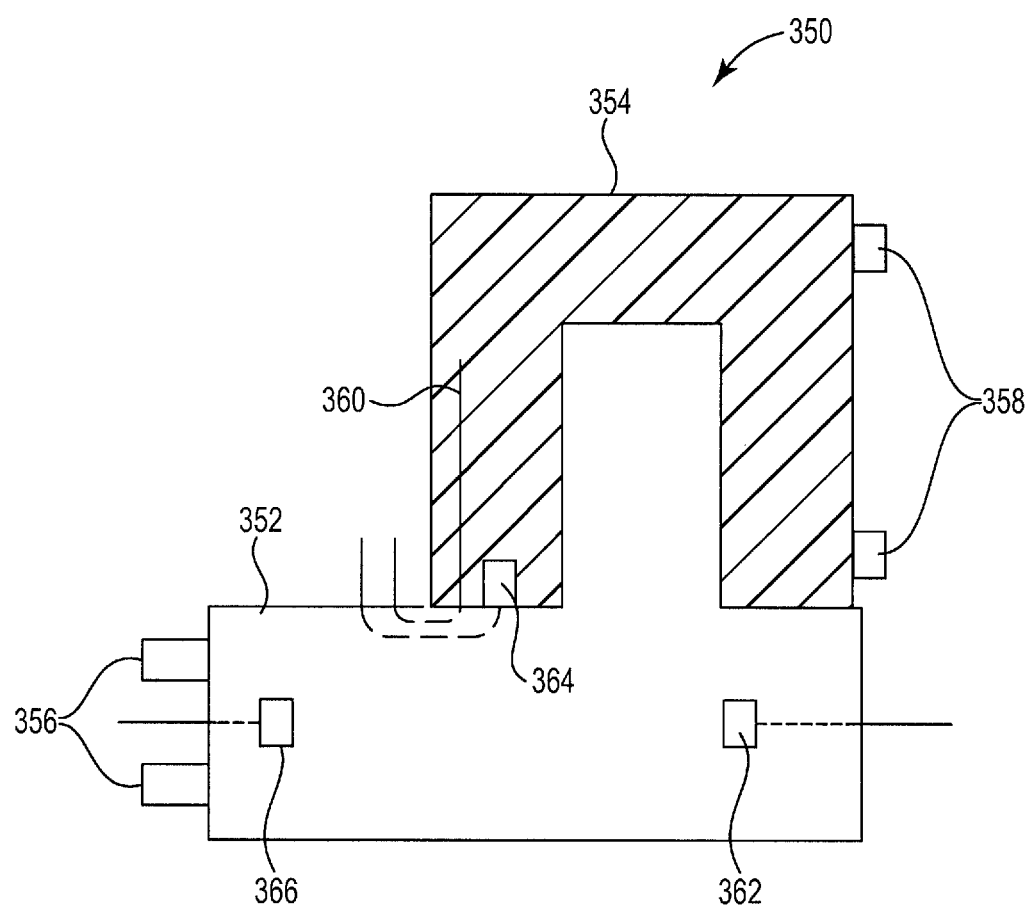
FIG. 5 is a diagram illustrating another heat exchanger, according to embodiments of the disclosure.

FIG. 5 is a diagram illustrating another heat exchanger 350, according to embodiments of the disclosure. The heat exchanger 350 includes a heat exchanger structure 352 and a container 354 that is sealed around the heat exchanger structure 352 in a fluid-tight connection. In some embodiments, the heat exchanger structure 352 is part of the primary circuit of the corresponding heater/cooler module, such that the heat exchanger structure 352 is a primary circuit module. In some embodiments, the container 354 is part of the secondary circuit of the corresponding heat transfer fluid circuit, such that the container 354 is a secondary circuit module. In some embodiments, the container 354 is part of the secondary circuit that contains the patient's blood or drugs or other fluids. In some embodiments, the container 354 is part of a secondary circuit that is directly the heat exchanger of an oxygenator.

The heat exchanger structure 352 includes fluidic connections 356 for fluidically connecting the primary circuit of the corresponding heater/cooler module to the heat exchanger structure 352. The fluidic connections 356 fluidically communicate a first fluid to the heat exchanger structure 352 through which the first fluid flows to achieve a first temperature of the heat exchanger structure 352, i.e., the first fluid flowing through the heat exchanger structure 352 facilitates heat transfer between the first fluid and the heat exchanger structure 352 to achieve a first temperature of the heat exchanger structure 352. In some embodiments, the heat exchanger structure 352 includes seals (not shown) for securing the container 354 to the heat exchanger structure 352 in a fluid-tight connection that prevents leakage of the second fluid.

The container 354 includes fluidic connections 358 for fluidically connecting the secondary circuit of the corresponding heat transfer fluid circuit to the container 354. The fluidic connections 358 fluidically communicate the second fluid through the container 354 and around the outside of the heat exchanger structure 352 to facilitate heat transfer between the heat exchanger structure 352 and the second fluid to achieve a second temperature of the second fluid, i.e., the second fluid flows through the container 354 and around the heat exchanger structure 352 separated by a heat conducting material in the container 354 to facilitate heat transfer between the heat exchanger structure 352 and the second fluid to achieve a second temperature of the second fluid. In some embodiments, the container 354 is a disposable container.

In some embodiments, the heat exchanger structure 352 includes an auxiliary electric heater 360 that is controlled to heat the second fluid. In some embodiments, the auxiliary electric heater 360 is electrically coupled to and controlled by the electronic control unit 208. In some embodiments, the heat exchanger structure 352 includes an auxiliary heater, such as an auxiliary electric heater, for heating the first fluid. In some embodiments, the heat exchanger structure 352 includes one or more auxiliary heaters, such as electric heaters or other suitable types of heaters. In some embodiments, the container 354 includes one or more auxiliary heaters, such as auxiliary electric heaters, controlled to heat the second fluid.

In some embodiments, the heat exchanger structure 352 includes a temperature sensor 362 to measure a temperature of the heat exchanger structure 352, with or without the second fluid in the container 354. In some embodiments, the temperature sensor 362 is electrically coupled to and read by the electronic control unit 208. In some embodiments, the heat exchanger 350 includes more than one temperature sensor for measuring the temperature of the heat exchanger structure 352.

In some embodiments, the heat exchanger structure 352 includes a temperature sensor 364 to measure a temperature of the second fluid in the container 354. In some embodiments, the temperature sensor 364 is electrically coupled to and read by the electronic control unit 208. In some embodiments, the heat exchanger 350 includes more than one temperature sensor for measuring the temperature of at least one of the first fluid and the second fluid. In some embodiments, the container 354 includes a temperature sensor to measure a temperature of the second fluid in the container 354.

In some embodiments, the heat exchanger structure 352 includes a temperature sensor 366 to measure a temperature of the first fluid. In some embodiments, the temperature sensor 366 is electrically coupled to and read by the electronic control unit 208.

Figure 6:
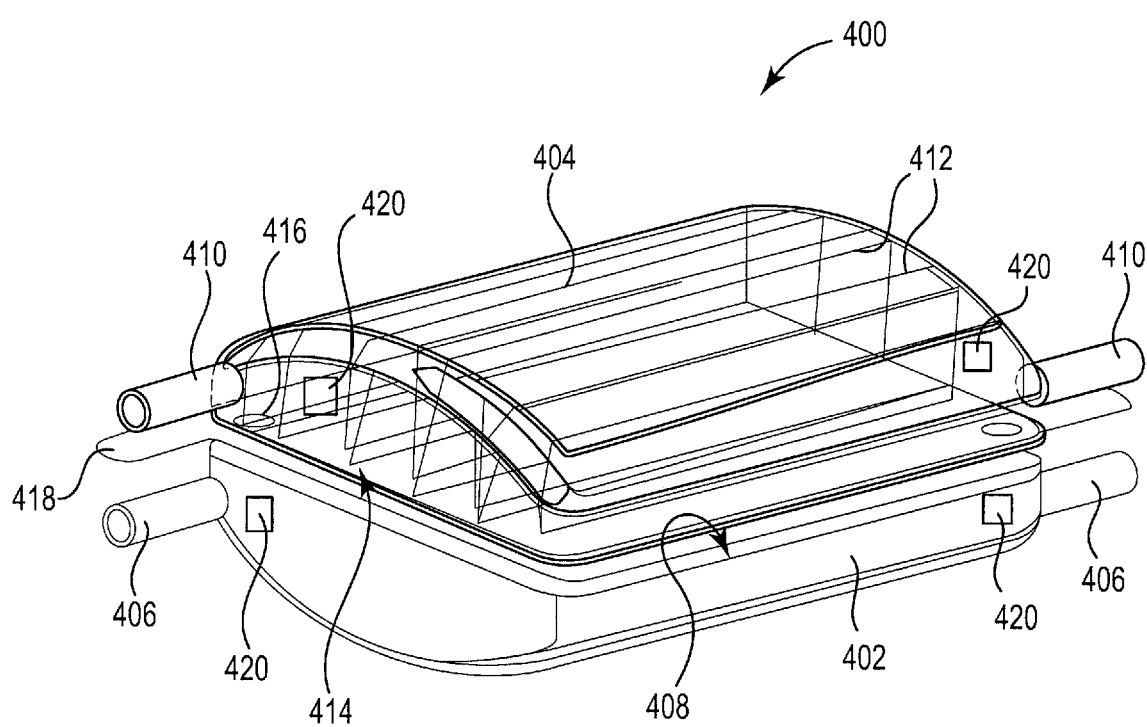
FIG. 6 is a diagram illustrating another heat exchanger, according to embodiments of the disclosure.

FIG. 6 is a diagram illustrating another heat exchanger 400, according to embodiments of the disclosure. The heat exchanger 400 includes a first heat exchanger module 402 and a second heat exchanger module 404. In some embodiments, the first heat exchanger module 402 is part of the primary circuit of the corresponding heater/cooler module, such that the first heat exchanger module 402 is a primary circuit module. In some embodiments, the second heat exchanger module 404 is part of the secondary circuit of the corresponding heat transfer fluid circuit, such that the second heat exchanger module 404 is a secondary circuit module.

The first heat exchanger module 402 includes inlet and outlet fluidic connections 406 for fluidically connecting the primary circuit of the corresponding heater/cooler module to the first heat exchanger module 402. The fluidic connections 406 fluidically communicate a first fluid to the first heat exchanger module 402 through which the first fluid flows to achieve a first temperature of the first heat exchanger module 402, i.e., the first fluid flowing through the first heat exchanger module 402 facilitates heat transfer between the first fluid and the first heat exchanger module 402 to achieve a first temperature of the first heat exchanger module 402. The first heat exchanger module 402 includes a flat side 408 that is situated in close proximity or next to the second heat exchanger module 404 to facilitate heat transfer between the first heat exchanger module 402 and the second heat exchanger module 404. In some embodiments, the flat side 408 of the first heat exchanger module 402 touches at least part of the second heat exchanger module 404 to facilitate heat transfer between the first heat exchanger module 402 and the second heat exchanger module 404. In some embodiments, the first heat exchanger module 402 includes a labyrinth of baffles or structures for causing the first fluid to circulate in the first heat exchanger module 402 to facilitate heat transfer between the first fluid and the first heat exchanger module 402. In some embodiments, the first heat exchanger module 402 is a disposable heat exchanger module. In some embodiments, the first heat exchanger module 402 is a non-disposable heat exchanger module that is part of the corresponding heater/cooler module.

The second heat exchanger module 404 includes inlet and outlet fluidic connections 410 for fluidically connecting the secondary circuit of the corresponding heat transfer fluid circuit to the second heat exchanger module 404. The fluidic connections 410 fluidically communicate the second fluid through the second heat exchanger module 404 and through a labyrinth of baffles or structures 412 to facilitate heat transfer between the second heat exchanger module 404 and the second fluid to achieve a second temperature of the second fluid, i.e., the second fluid flows through the second heat exchanger module 404 to facilitate heat transfer between the second heat exchanger module 404 and the second fluid to achieve a second temperature of the second fluid. The second heat exchanger module 404 includes a flat side 414 that is situated in close proximity or next to the flat side 408 of the first heat exchanger module 402 to facilitate heat transfer between the first heat exchanger module 402 and the second heat exchanger module 404, which then transfers heat to/from the second heat exchanger module to the second fluid to achieve the second temperature of the second fluid. In some embodiments, the flat side 408 of the first heat exchanger module 402 touches at least part of the flat side 414 of the second heat exchanger module 404 to facilitate heat transfer between the first heat exchanger module 402 and the second heat exchanger module 404. In some embodiments, the second heat exchanger module 404 is a disposable heat exchanger module. In some embodiments, the second heat exchanger module 404 is a non-disposable heat exchanger module that is part of one of the corresponding heater/cooler module or the corresponding heat transfer circuit module. In some embodiments at least one of the first heat exchanger module 402 and the second heat exchanger module 404 is referred to as a plate heat exchanger or a plate heat exchanger module.

The first heat exchanger module 402 and the second heat exchanger module 404 include a positioning mechanism 416 for situating and positioning the first and second heat exchanger modules 402 and 404 together. In some embodiments, the positioning mechanism 416 includes a safety interlock to prevent operation if the first and second heat exchanger modules 402 and 404 are not interfaced properly and, in some embodiments, to provide a warning signal to the operator. In some embodiments, one of the first heat exchanger module 402 and the second heat exchanger module 404 includes a pin, such as at one or more corners, and the other includes one or more holes configured to receive the one or more pins for placement. In some embodiments, the dimensions of the positioning mechanism 416, such as a positioning pin, are detected by the electronic control unit 308 and used to adapt the performance parameters of the system to the specific first and/or second heat exchanger modules 402 and 404 being used.

In some embodiments, the heat exchanger 400 includes one or more auxiliary heaters, such as auxiliary electric heater 418, to heat the second fluid and, in some embodiments, to more precisely regulate the amount of energy transferred to the target device and/or a patient. In some embodiments, at least one of the auxiliary electric heaters 418 is situated between the first heat exchanger module 402 and the second heat exchanger module 404 and controlled to transfer heat to the second heat exchanger module 404 and the second fluid. In some embodiments, at least one of the auxiliary electric heaters is situated on or in one or more of the first heat exchanger modules 402 and controlled to transfer heat to the second fluid. In some embodiments, the first heat exchanger module 402 includes at least one auxiliary heater, such as auxiliary electric heater 418, for heating the first fluid. In some embodiments, the second heat exchanger module 404 includes at least one auxiliary heater, such as auxiliary electric heater 418, for heating the second fluid. In some embodiments, at least one of the auxiliary electric heaters 418 can be used during thermal disinfection to dry and thermally disinfect one or more of the first and second heat exchanger modules 402 and 404. In some embodiments, at least one of the auxiliary electric heaters 418 is electrically coupled to and controlled by an electronic control unit, such as the electronic control unit 208. In some embodiments, one or more of the auxiliary heaters are auxiliary heater/coolers, such as Peltier type heater/coolers, for transferring heat to and/or from the second fluid.

In some embodiments, the heat exchanger 400 includes one or more temperature sensors 420 to measure a temperature of at least one of the first fluid and the second fluid. In some embodiments, the heat exchanger 400 includes at least one temperature sensor 420 situated near at least one of the inlet and the outlet fluidic connections 406 to measure the temperature of the first fluid. In some embodiments, the heat exchanger 400 includes at least one temperature sensor 420 situated near at least one of the inlet and outlet fluidic connections 410 to measure the temperature of the second fluid, where the temperature of the second fluid at the outlet fluidic connection 410 measures the temperature of the fluid flowing to the target device and the temperature of the second fluid at the inlet fluidic connection 410 can be used to measure or calculate the amount of energy transferred to the target device. In some embodiments, the heat exchanger 400 includes one or more temperature sensors 420 configured to measure a temperature of at least one of the first and second heat exchanger modules 402 and 404, with or without fluid in the at least one of the first and second heat exchanger modules 402 and 404. In some embodiments, one or more of the temperature sensors 420 is electrically coupled to and read by the electronic control unit 208. In some embodiments, the temperature sensors 420 extend into the first and/or second heat exchanger modules 402 and 404 to measure the temperature of the first and/or second fluids, respectively.

Figure 7:
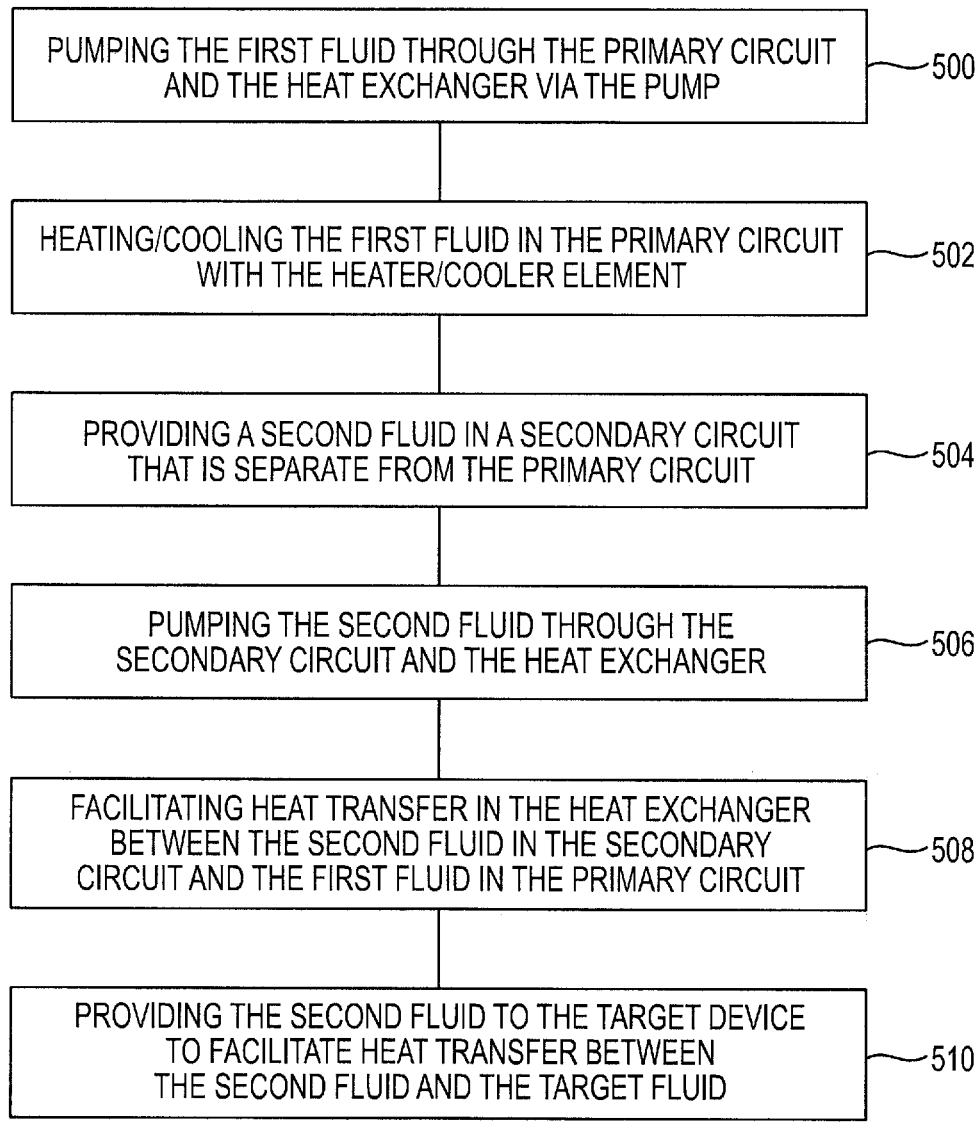
FIG. 7 is a flow chart diagram illustrating a method of heating/cooling a target fluid in a target device via a heater/cooler module, according to embodiments of the disclosure.

FIG. 7 is a flow chart diagram illustrating a method of heating/cooling a target fluid in a target device via a heater/cooler module, according to embodiments of the disclosure.

The heater/cooler module includes a first fluid in a primary circuit, a pump, a heater/cooler element, and a heat exchanger.

At 500, the method includes pumping the first fluid through the primary circuit and the heat exchanger via the pump. At 502, the method includes heating/cooling the first fluid in the primary circuit with the heater/cooler element. In some embodiments, the heater/cooler element includes a heat pump. In some embodiments, heating/cooling the first fluid includes heating/cooling the first fluid in the primary circuit with an auxiliary heat exchanger in the heater/cooler module, where the auxiliary heat exchanger is configured to receive a third fluid to facilitate heat transfer between the third fluid and the first fluid in the primary circuit. In some embodiments, heating/cooling the first fluid includes heating/cooling the first fluid in the primary circuit with a thermoelectric heater/cooler, such as a Peltier heater/cooler, coupled to the heat exchanger.

At 504, the method includes providing a second fluid in a secondary circuit that is separate from the primary circuit, such that the first fluid and the second fluid are maintained as separate fluids. At 506, the method includes pumping the second fluid through the secondary circuit and the heat exchanger and, at 508, facilitating heat transfer in the heat exchanger between the second fluid in the secondary circuit and the first fluid in the primary circuit. In some embodiments, facilitating heat transfer between the second fluid in the secondary circuit and the first fluid in the primary circuit includes pumping the first fluid through a heat exchanger coil that is part of the primary circuit and situated in the heat exchanger, and pumping the second fluid through a container that is sealed around the heat exchanger coil, such that the second fluid flows around the heat exchanger coil. In some embodiments, facilitating heat transfer between the second fluid in the secondary circuit and the first fluid in the primary circuit includes pumping the first fluid through a heat exchanger structure that is part of the primary circuit and situated in the heat exchanger, and pumping the second fluid through a container that is sealed around the heat exchanger structure, such that the second fluid flows around the heat exchanger structure. In some embodiments, facilitating heat transfer between the second fluid in the secondary circuit and the first fluid in the primary circuit pumping the first fluid through a first plate heat exchanger that is part of the primary circuit and situated in the heat exchanger, pumping the second fluid through a second plate heat exchanger that is part of the secondary circuit and the heat transfer fluid circuit, and facilitating heat transfer between the first plate heat exchanger and the second plate heat exchanger to heat/cool the second fluid.

At 510, the method includes providing the second fluid to the target device to facilitate heat transfer between the second fluid and the target fluid. In some embodiments, the method also includes heating at least one of the first fluid in the heat exchanger and the second fluid in the heat exchanger with one or more auxiliary electric heaters coupled to the heat exchanger.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system for heating or cooling a patient's blood during a procedure involving extracorporeal blood circulating, the system comprising:
  a heater/cooler module including a first pump and a first heater/cooler element fluidly coupled to a primary circuit including a heating circuit path and a separate cooling circuit path, and configured to heat and/or cool a first fluid in the primary circuit, wherein each of the separate heating and cooling circuit paths are fluidly coupled to the first heater/cooler element;
  a heat transfer fluid circuit including a secondary circuit configured to provide a second fluid to a target device containing blood therein to heat and/or cool the blood; and
  a heat exchanger including at least part of the primary circuit through which the first fluid flows and at least part of the secondary circuit through which the second fluid flows to facilitate heat transfer between the first fluid and the second fluid, wherein the primary circuit and the secondary circuit are separate circuits, such that the first fluid and the second fluid remain separated in the system.

2. The system of claim 1, wherein the primary circuit is a permanent part of the heater/cooler module and the at least part of the secondary circuit is disposable.

3. The system of claim 1, wherein the heat transfer fluid circuit is a single use disposable circuit.

4. The system of claim 1, including at least one of:
  two or more heat exchangers;
  two or more heater/cooler modules; and
  two or more heat transfer fluid circuits.

5. The system of claim 1, wherein the heat exchanger includes one or more temperature sensors configured to measure a temperature of the heat exchanger.

6. The system of claim 1, wherein the target device includes an oxygenator and a heat exchanger.

7. The system of claim 6, comprising a first temperature sensor configured to take temperature measurements of the blood and a second temperature sensor configured to take temperature measurements of at least one of the first fluid and the second fluid, wherein the system is configured to maintain a predefined temperature offset between the blood and the at least one of the first fluid and the second fluid.

8. The system of claim 1, wherein the heat exchanger includes a first module configured to receive the first fluid and a disposable module configured to receive the second fluid; and wherein the first module includes one or more auxiliary electric heaters to heat at least one of the first fluid and the second fluid or a temperature sensor configured to measure the temperature of at least one of the first fluid and the second fluid.

9. The system of claim 8, wherein the disposable module includes one or more auxiliary electric heaters to heat at least one of the first fluid and the second fluid.

10. A method of heating and/or cooling blood in a target device via a heater/cooler module including a first fluid in a primary circuit, an integrated pump, a first heater/cooler element, and a heat exchanger, the method comprising:
  pumping the first fluid through the primary circuit and the heat exchanger via the pump, the primary circuit including a heating circuit path and a separate cooling circuit path;
  heating and/or cooling the first fluid in the primary circuit with the first heater/cooler element, wherein each of the separate heating and cooling circuit paths are fluidly coupled to the first heater/cooler element such that heating the first fluid in the primary circuit and cooling the first fluid in the primary circuit each involve pumping the first fluid through the first heater/cooler element;

providing a second fluid in a secondary circuit that is separate from the primary circuit, such that the first fluid and the second fluid are maintained as separate fluids;

pumping the second fluid through the secondary circuit and the heat exchanger;

facilitating heat transfer in the heat exchanger between the second fluid in the secondary circuit and the first fluid in the primary circuit; and providing the second fluid to the target device to facilitate heat transfer between the second fluid and the blood.

11. The method of claim 10, wherein heating and/or cooling the first fluid comprises:

heating and/or cooling the first fluid in the primary circuit with a heat pump; or heating and/or cooling the first fluid comprises heating and/or cooling the first fluid in the primary circuit with an auxiliary heat exchanger in the heater/cooler module, the auxiliary heat exchanger configured to receive a third fluid to facilitate heat transfer between the third fluid and the first fluid in the primary circuit; or heating and/or cooling the first fluid comprises heating and/or cooling the first fluid in the primary circuit with a thermoelectric heater/cooler coupled to the heat exchanger.

12. The method of claim 10, comprising heating at least one of the first fluid in the heat exchanger and the second fluid in the heat exchanger with one or more auxiliary electric heaters coupled to the heat exchanger.

13. The method of claim 10, wherein facilitating heat transfer between the second fluid in the secondary circuit and the first fluid in the primary circuit comprises:

pumping the first fluid through a heat exchanger coil that is part of the primary circuit and situated in the heat exchanger; and pumping the second fluid through a container that is sealed around the heat exchanger coil, such that the second fluid flows around the heat exchanger coil.

14. The method of claim 10, comprising regulating a temperature of the blood in the target device by measuring a fluid temperature of at least one of the first fluid and the second fluid.

15. The method of claim 10, comprising maintaining a predefined temperature offset between the blood in the target device and at least one of the first fluid and the second fluid.

16. A system for heating or cooling a patient's blood during a procedure involving extracorporeal blood circulating, the system comprising:

a heater/cooler module including a first pump and a first heater/cooler element fluidly coupled to a primary circuit including a heating circuit path and a separate cooling circuit path, and configured to heat and/or cool a first fluid in the primary circuit, wherein each of the separate heating and cooling circuit paths are fluidly coupled to the first heater/cooler element such that the first fluid when heated by the first heater/cooler element flows from the first heater/cooler element into the heating circuit path and the first fluid when cooled by the first heater/cooler element flows from the first heater/cooler element into the cooling circuit path;

a heat transfer fluid circuit including a secondary circuit configured to provide a second fluid to a target device containing blood therein to heat and/or cool the blood; and a heat exchanger including at least part of the primary circuit through which the first fluid flows and at least part of the secondary circuit through which the second fluid flows to facilitate heat transfer between the first fluid and the second fluid, wherein the primary circuit and the secondary circuit are separate circuits, such that the first fluid and the second fluid remain separated in the system.

17. The system of claim 16, wherein the heating circuit path is fluidly connected between the first heater/cooler element and the first pump.

18. The system of claim 17, wherein the cooling circuit path is fluidly connected between the first heater/cooler element and the first pump.

* * * * *